United States Patent [19]

Agar et al.

[11] Patent Number: 5,788,812
[45] Date of Patent: Aug. 4, 1998

[54] METHOD OF RECOVERING FURFURAL FROM ORGANIC PULPING LIQUOR

[76] Inventors: Richard C. Agar, 11823 Woodvale Ct., Springdale, Ohio 45246; Jairo H. Lora, 7 Camby Chase, Media, Pa. 19063; Malcolm Cronlund, 434 Saddlebrook Cir., Chester Springs, Pa. 19425; Chih Fae Wu, 1607 Bow Tree Dr., West Chester, Pa. 19380; Gopal C. Goyal, 126 Sycamore Ct., Collegeville, Pa. 19426; Stephen R. Winner, 180 Mattson Rd., Boothwyn, Pa. 19061; Mikhail N. Raskin, 606 S. Gulph Ct. #217, King of Prussia, Pa. 19406; Raphael Katzen, 2868 Alpine Ter., Cincinnati, Ohio 45208; Ron LeBlanc, c/o Saudi Aramco, Box 4511 Ras Tan Ura, via Dhahran, Saudi Arabia, 31311

[21] Appl. No.: 488,306

[22] Filed: Jun. 7, 1995

Related U.S. Application Data

[60] Division of Ser. No. 11,329, Jan. 29, 1993, which is a continuation-in-part of Ser. No. 649,683, Feb. 1, 1991, abandoned, which is a continuation-in-part of Ser. No. 232,298, Aug. 15, 1988, abandoned, which is a division of Ser. No. 940,460, Dec. 11, 1986, Pat. No. 4,764,596, which is a continuation-in-part of Ser. No. 795,069, Nov. 5, 1985, abandoned.

[51] Int. Cl.$^6$ .................... D21C 3/20; D21C 11/00
[52] U.S. Cl. .................... 162/16; 162/37; 162/39; 162/77; 549/490
[58] Field of Search .................... 162/14, 16, 17, 162/29, 77, 40, 68, 37, 39; 549/485, 500, 489, 490; 530/507

[56] References Cited

U.S. PATENT DOCUMENTS

| | | |
|---|---|---|
| 1,856,567 | 5/1932 | Kleinert et al. . |
| 2,153,316 | 4/1939 | Sherrard et al. . |
| 2,156,159 | 4/1939 | Olsen et al. . |
| 2,331,154 | 10/1943 | Adkins . |
| 2,380,448 | 1/1945 | Katzen . |

(List continued on next page.)

FOREIGN PATENT DOCUMENTS

| | | |
|---|---|---|
| 936395 | 11/1973 | Canada . |
| 938820 | 12/1973 | Canada . |
| 946800 | 5/1974 | Canada . |

(List continued on next page.)

OTHER PUBLICATIONS

Williamson, "Repap's Alcell process: How it works and what it offers"; Pulp and Paper Canada ; Dec. 1978; pp. 47–49.

Lora et al., Proceedings of the Tappi 1984 Research & Develop. Conf.; ,Appleton, WI (Sep. 30–Oct. 3 1984) 162–77.

(List continued on next page.)

*Primary Examiner*—Steven Alvo
*Attorney, Agent, or Firm*—Reed Smith Shaw & McClay LLP

[57] ABSTRACT

This invention provides for the recovery of lignin and other by-products from the pulping of fibrous plant material. In accordance with this invention, solvents and filtrates are recovered and recycled for reuse. This results in significant solvent and energy savings. Filtrates from the bleaching and delignification of the pulp are recycled for reuse in pulping, separation, and recovery of lignin and other by-products which results in significant energy savings and mitigation if not the elimination of pollution typically associated with bleaching. This invention also relates to products derived from the process and apparatus for carrying out the process. Lignins of various molecular weights and by-products of the pulping process are also recovered. The lignins are precipitated in high yields and at a high rate from a black liquor produced by pulping wood at high temperature and pressures. As a by-product of this process a purified furfural product is recovered. This furfural may be recycled for use in the recovery of the low molecular weight lignin of this process.

4 Claims, 10 Drawing Sheets

U.S. PATENT DOCUMENTS

| | | |
|---|---|---|
| 3,223,697 | 12/1965 | Ball . |
| 3,298,899 | 1/1967 | Laakso . |
| 3,303,088 | 2/1967 | Gessner . |
| 3,434,920 | 3/1969 | Green . |
| 3,530,034 | 9/1970 | Erickson . |
| 3,532,594 | 10/1970 | Richter . |
| 3,585,104 | 6/1971 | Kleinert . |
| 3,811,994 | 5/1974 | Ostberg . |
| 3,992,248 | 11/1976 | Hurter . |
| 4,071,399 | 1/1978 | Prough . |
| 4,096,027 | 6/1978 | Sherman . |
| 4,100,016 | 7/1978 | Diebold et al. . |
| 4,162,933 | 7/1979 | Sherman et al. . |
| 4,190,490 | 2/1980 | Tomlinson . |
| 4,231,842 | 11/1980 | Oala . |
| 4,274,913 | 6/1981 | Kikuiri et al. . |
| 4,276,167 | 6/1981 | Richter et al. . |
| 4,375,410 | 3/1983 | Richter et al. . |
| 4,395,543 | 7/1983 | Wang et al. . |
| 4,401,514 | 8/1983 | Kanzler et al. . |
| 4,430,029 | 2/1984 | Richter et al. . |
| 4,470,876 | 9/1984 | Beaupre et al. . |
| 4,496,426 | 1/1985 | Baumeister et al . |
| 4,511,433 | 4/1985 | Tournier et al. . |
| 4,516,887 | 5/1985 | Richter et al. . |
| 4,529,482 | 7/1985 | Richter et al. . |
| 4,584,057 | 4/1986 | Rowe et al. . |
| 4,592,804 | 6/1986 | Noreus et al. . |
| 4,595,456 | 6/1986 | Andersson . |
| 4,608,121 | 8/1986 | Ostman . |
| 4,632,729 | 12/1986 | Laakso . |
| 4,670,098 | 6/1987 | Thorsell et al. . |
| 4,693,785 | 9/1987 | Laakso . |
| 4,746,404 | 5/1988 | Laakso . |
| 4,764,401 | 8/1988 | Roberts et al. . |
| 4,764,596 | 8/1988 | Lora et al. . |
| 4,767,500 | 8/1988 | Patt et al. . |
| 4,790,905 | 12/1988 | Nivelleau de La Brumere et al. . |
| 4,814,042 | 3/1989 | MacLeod et al. . |
| 4,836,893 | 6/1989 | Gloersen . |
| 4,966,650 | 10/1990 | DeLong et al. . |
| 4,971,657 | 11/1990 | Avignon et al. ............................ 162/77 |
| 5,382,321 | 1/1995 | Fagerlind et al. . |

FOREIGN PATENT DOCUMENTS

| | | |
|---|---|---|
| 1054757 | 5/1979 | Canada . |
| 1100266 | 5/1981 | Canada . |
| 1107920 | 9/1981 | Canada . |
| 1121638 | 4/1982 | Canada . |
| 1130061 | 8/1982 | Canada . |
| 1141575 | 2/1983 | Canada . |
| 1147105 | 5/1983 | Canada . |
| 1153232 | 9/1983 | Canada . |
| 1222898 | 6/1987 | Canada . |
| 1241859 | 9/1988 | Canada . |
| 1250480 | 2/1989 | Canada . |
| 0018562 | 11/1980 | European Pat. Off. . |
| 0043342 | 1/1982 | European Pat. Off. . |
| 0052382 | 5/1982 | European Pat. Off. . |
| 0161330 | 11/1985 | European Pat. Off. . |
| 0403068 | 12/1990 | European Pat. Off. . |
| 0472820 | 3/1992 | European Pat. Off. . |
| 9320279 | 11/1993 | European Pat. Off. . |
| 24032 | 7/1950 | Finland . |
| 2855052 | 6/1980 | Germany . |
| 5279560 | 7/1977 | Japan . |
| 5836291 | 3/1983 | Japan . |
| 9213849 | 8/1992 | WIPO . |

OTHER PUBLICATIONS

Elmore; "Where Energy May Be Conserved in Continuous Digestor Operation"; Pulping Process; pp. 30, 31, 1981.

"Pressure Diffuser Type 30"Trade Information; May 1986; Kamyr.

Marchessault et al.; "Monomers and Oligomers from Wood"; Pulp. Pap. Mag. Can. Trans.. (1980).

Marchessault et al. Characterization of Aspen Exploded Wood Lignin: Can. J. Chem. 60, 2372–2382 (1982).

Lora et al. "Organosolv Pulping: A Versatile Approach to Wood Refining"Tappi Proceedings, 1984 Research and Development Conference, pp. 94, 96 (1984).

Laxen, T., The Characteristics of Organosolv Pulping Discharges Paper JA PUU, pp. 417–421 (May 1987).

Myerly et al., "The Forest Refinery" Chemtech, 11, p. 186–192.

Rydholm, Pulping Processes, Interscience Publishers, New York, p. 672–673 (1971).

Glasser, "Potential Role of Lignin in Tomorrow's Wood Ulitization Technologies", Forest Prod. J. vol. 31, No. 3 pp. 24–29 (Mar., 1981).

Lora et al. "Characteristics and Potential Applications of Lignin Produced by an Organosoly Pulping Process", Properties and Materials, 1989 American Chemical Society.

Perry, Chemical Engineer handbook, McGraw Hill Book Co., New York, Fourth Edition, pp. 21–12 to 21–13 (1963).

Pulp & Paper Week; "Repap, Kamyr working on Alcell Pulp Mills" Miller Freeman Publications Inc. May 1990.

Smook, "Handbook for Pulp & Paper Technologies", Canadian Pulp and Paper Association, pp. 80–88 (1986).

"Kamyr Technology", Kamyr Inc., pp. 38,43, 71–94 (Mar. 1988).

Katzen et al.,"The Alcohol Pulping & Recovery Process" CEP; pp. 62–67 (Feb. 1980).

Aziz et al. "Organosolv Pulping —a review" Tappi Journal; pp. 169–175 (Mar. 1989).

"Chemical Process Synthesis and Engineering Design" Safety In Chemical Plant Design pp. 150–153.

Katzen et al. "Alcohol Pulping Appears Feasible For Small Incremental Capacity" Pulp & Paper; pp. 144–149 (Aug. 1980).

Kleinert et al; "Organosolv Pulping with Aqueous Alcohol" pp. 221–224.

Wells; "Safety in Process Plant Design" pp. 76, 82, 204, 238–257.

Biological Energy Corp., "Alcohol Pulping and Recovery Process" Jun. 1984.

Williamson: "Repap's Alcell Process: How It Works and What it offers" Pulp & Paper Canada; pp. 47–49 (1987).

Ingruber et al. "Sulfite Science & Technology" Pulp and Paper Manufacture , Third Edition, vol. 4, p. 111 (1983).

Paszner et al. "Organosolv Pulping —Acidic Catalysis options and their effect on fiber quality and delignification" Tappi Journal, p. 135–142 (Feb. 1989).

E.K. Pye, "The Alcell Process" Proceedings —1989 Solvent Pulping Conference; Oct. 1989, pp. 16–32.

Econotech Services Limited "Use of Organosolv Processes Renewable Energy Division" Sep. 1986.

Rydholm, S. "Continuous Pulping Processes", Sep. 1968, pp. 33–34, 107.

G. Dahlman et al "The Organocell Process —Pulping with the environment in Mind" Tappi Journal , Apr. 1990, pp. 237–240.

"APR Process Schematic Diagram Equipment Identification".

Goyal et al Autocatalyzed Organosolv Pulping of North American Hardwoods Effect of Pulping Conditions on Pulp Properties and Characteristics of the Soluble and Residual Lignin. Tappi Proceedings; pp.627–635 (1991).

A. Harrison, "Repap Produces High Quality Pulp at Newcastle with Alcell Process" Pulp & Paper , Feb. 1991 pp. 116–119.

T. McDonough, The Chemistry of Organosolv Delignification Tappi Journal, Aug. 1993 pp. 186–193.

METHOD OF RECOVERING FURFURAL FROM ORGANIC PULPING LIQUOR

CROSS-REFERENCE TO RELATED APPLICATION

This is a divisional of application Ser. No. 08/011,329 filed on Jan. 29, 1993, which is a continuation-in-part of application Ser. No. 07/649,683, filed Feb. 1, 1991 entitled "PULPING OF LIGNOCELLULOSIC MATERIALS AND RECOVERY OF RESULTANT BY-PRODUCTS", now abandoned, which is a continuation-in-part of application Ser. No. 07/232,298, filed Aug. 15, 1988, entitled "LIGNIN RECOVERY", now abandoned, which is a divisional application of Ser. No. 06/940,460, filed Dec. 11, 1986, now U.S. Pat. No. 4,764,596 entitled "RECOVERY OF LIGNIN", which is a continuation-in-part of application Ser. No. 06/795,069, filed Nov. 5, 1985 entitled "PROCESS FOR LIGNIN RECOVERY" now abandoned.

BACKGROUND OF THE INVENTION

This invention generally relates to the pulping of fibrous plant materials including lignocellulosic materials and the recovery of the resultant by-products resulting from the pulping process. More specifically, this invention relates to pulping of fibrous plant materials in a water miscible organic solvent (e.g. lower aliphatic alcohol) and recovering and recycling the organic solvent and various by-products of the pulping process (e.g. cellulose, lignin, furfural hemicellulose and sugars). Pulping of the fibrous plant materials and the recovery of the resultant by-products may be carried out in either continuous or batch processes.

Processes for treating wood with organic solvents, such as alcohol, to separate the wood's lignin, hemicellulose, sugar and cellulose fractions are now well known. See, for example, Kleinert et al U.S. Pat. No. 1,856,567 and Kleinert U.S. Pat. No. 3,585,104. Such solvent pulping processes have appeared to be attractive alternatives to conventional chemical pulping processes, such as kraft and sulfite, which suffer from relatively high equipment cost and pollution problems.

One solvent pulping process, disclosed in Diebold et al U.S. Pat. No. 4,100,016, has appeared to be particularly attractive in providing highly efficient recovery of its alcohol solvent, separation of the cellulose and lignin fractions of wood, and recovery of cellulose pulp with no appreciable air or water pollution or solid waste products. This patented process has also provided hardwood pulps with yields, Kappa numbers, viscosities, fiber strengths and bleachability characteristics that are equal to or better than kraft and sulfite hardwood pulps.

However, the recovery of lignin and other by-products from the alcohol/water black liquor, generated by the solvent pulping process of Diebold et al U.S. Pat. No. 4,100,016, has been relatively inefficient and difficult to control. Lignin has been recovered from the black liquor in this patent by first stripping (preferably vacuum stripping) alcohol from the black liquor and then separating the lignin which precipitates from the stripper bottoms or tails (preferably by thickening and then centrifuging the settled solids from the stripper bottoms). However, a portion of the lignin has tended to precipitate as a sticky tar or gum on the internal surfaces of the stripper, thereby fouling the stripper and reducing its efficiency in recovery of alcohol from the black liquor. The lignin also has tended to precipitate from the stripper bottoms as a sticky amorphous mass which has been difficult to handle and has required substantial crushing to convert the lignin mass into a powder.

As a result, more efficient ways have been sought for removing lignin and other by-products from the black liquor produced by a solvent pulping process such as is disclosed in Diebold et al U.S. Pat. No. 4,100,016. One method has involved precipitating lignin from the alcohol/water black liquor by diluting it with water. See Rydholm, "Pulping Processes", pp. 672–673, Interscience Publishers, New York (1971). However, this method has resulted in very slow settling rates of the lignin, and in some cases, a very stable colloidal suspension of the lignin has been formed which has been difficult to filter or centrifuge. There has been a continuing need, therefore, for a relatively simple way of recovering lignin and other by-products from an alcohol/water black liquor in high yields and at high rates in an easy to handle and useful form. Moreover, while solvent pulping processes produce hardwood pulps that are comparable in strength, brightness and cleanliness to kraft pulps produced from the same wood species, the resultant pulp from such pulping operations contains higher residual lignin in the pulp. Therefore pulps resulting from solvent pulping processes generally have a higher residual lignin content as measured by the pulp kappa number, and require, among other things, a large quantity of bleaching chemicals to produce satisfactorily bleached pulps. The increased use of large quantities of bleaching chemicals using conventional bleaching techniques created a need for devising new bleaching methods and/or systems for the disposal or recycling of these chemicals. Further, solvent pulping processes produce as a by-product furfural which can accumulate in the pulping solvent and interfere with delignification. There is therefore a distinct need for methods, apparatus and/or systems, which provide energy efficient, environmentally attractive and economically feasible means for pulping fibrous plant materials and recovering the by-products of the pulping process.

The Lora et al. U.S. Pat. No. 4,764,596, addresses some of the foregoing problems. In Lora, lignin and other by-products of the pulping process are recovered from a "black liquor" produced when wood or other fibrous plant materials are contacted with a water miscible organic solvent (e.g. ethanol/water solvent) at elevated temperatures and pressures. The Lora process successfully allows for the recovery of many by-products, including most of the lignin liberated during pulping. It has also been discovered through improvements of the Lora patent as set forth herein that additional by-products, including lower molecular weight lignin and furfural, may be recovered while simultaneously increasing the overall energy efficiency of the process, reducing the consumption of solvent required throughout the system and significantly reducing or eliminating environmentally undesirable effluent.

The invention described herein includes the foregoing improvements and additionally accelerates delignification of the black liquor and allows for the recovery of additional by-products and streams from the pulping process. This invention not only recovers furfural from the residual black liquor filtrates produced during lignin recovery but uses the furfural to recover low molecular weight lignin by recycling it into the system. Also incorporated herein is a system which not only accommodates novel bleaching techniques but provides for the recycling of bleaching effluent filtrates, which accelerate delignification and mitigate against pollution.

SUMMARY OF THE INVENTION

This invention provides for the recovery of lignin and other by-products from pulping of fibrous material. In accordance with this invention, solvents and filtrates are recovered and recycled for reuse. This results in a significant solvent and energy savings.

In accordance with this invention, filtrates from the bleaching and delignification of the pulp of this invention are recycled for reuse in the continuous or batch pulping, separation and recovery of lignin and other by-products. The reuse of the bleaching filtrates results in accelerated delignification and greater operating efficiency. The net result is a significant energy savings and mitigation if not the elimination of pollution typically associated with bleaching.

In accordance with this invention, lignin is recovered from a black liquor comprising a solution of lignin, hemicellulose, and a water miscible organic solvent by precipitating lignin solids by diluting the black liquor with water and acid under conditions to form a diluted residual black liquor including a diluted residual black liquor supernatant and precipitated lignin solids which are free from the formation of tarry lignin precipitates and recovering the lignin by separating the lignin solids from the diluted residual black liquor supernatant.

In accordance with another aspect of this invention, a novel lignin is precipitated by the process of this invention. A preferred lignin is characterized by: a number average molecular weight of about 700 to 1500 g/mol, a glass transition temperature of about 700 to 170° C., a polydispersity of less than about 4 and a methoxyl content approximately equal to that of native lignin.

In accordance with another aspect of this invention, a novel low molecular weight lignin is obtained. A preferred lignin is characterized by: a low average molecular weight in the range of less than 600 g/mol, a glass transition in the range of from about 24° to 75° C. and a syringhaldehyde to vanillin molar ratio of about 2.7:1 to 5.3:1 especially as it relates to hardwoods. It is expected that a more soluble lignin having a novel structure is produced.

In accordance with another aspect of this invention, a purified furfural product is recovered. The furfural product contains from about 95 to 98% furfural, from about 0.1 to 0.5% ethanol and from about 0.1 to 2% water.

Other aspects of this invention will be apparent from a reading of the remainder of this specification, including the drawings and claims.

DETAILED DESCRIPTION OF THE PREFERRED EMBODIMENTS

Figure 1:
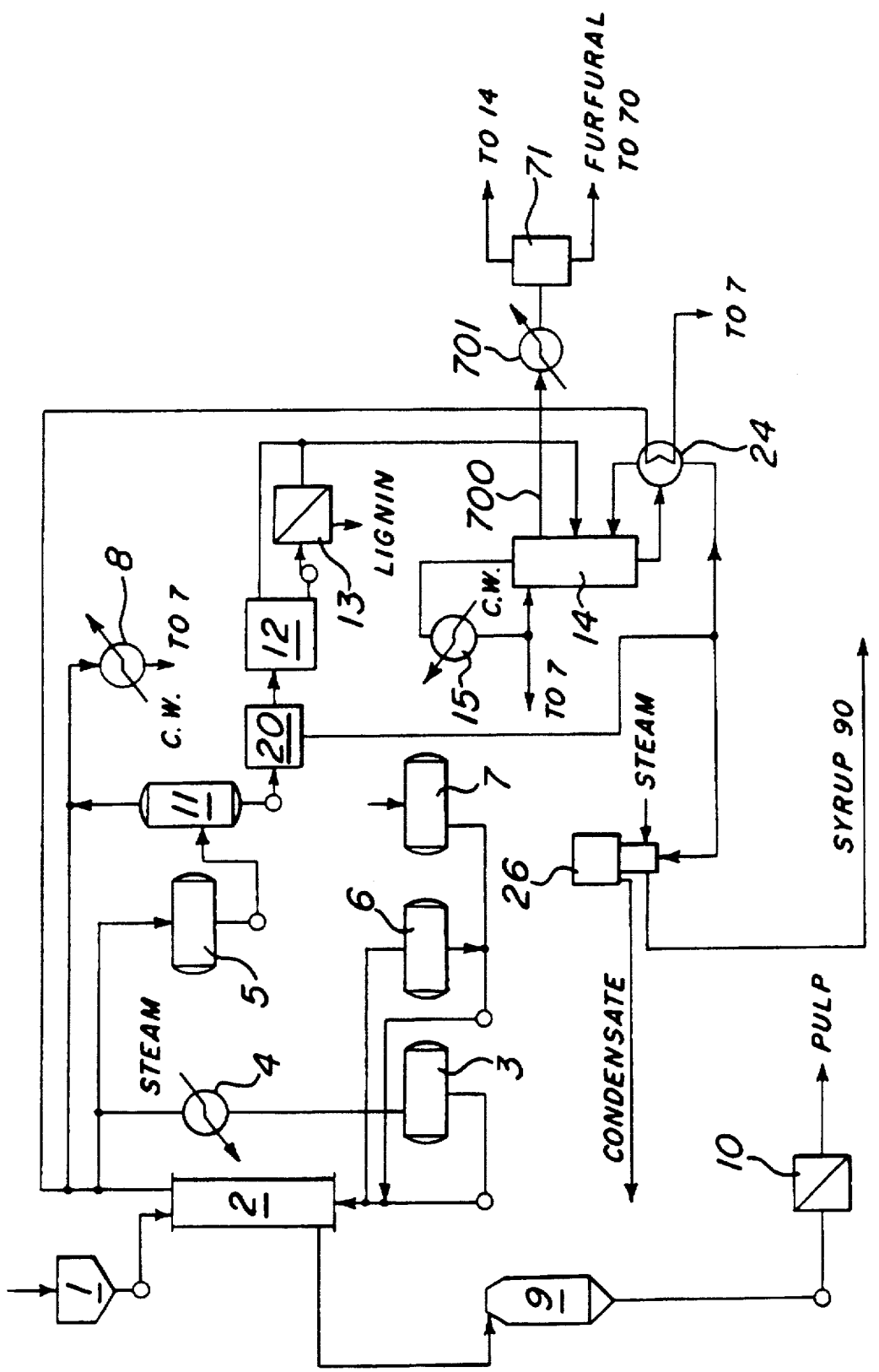
FIGS. 1, 11 and 12 represent batch processes for producing cellulose pulp from fibrous plant materials by treating the fibrous plant materials with an aqueous alcohol solvent, and for recovering lignin and other by-products from the alcohol/water black liquor.

The process shown in FIG. 1 initially involves pulping a batch of wood chips or other fibrous plant materials that are loaded from a hopper 1 into an extractor 2. The extractor 2 is operated in accordance with Diebold et al U.S. Pat. No. 4,100,016 at an elevated temperature (e.g., about 180° to 210° C.) and an elevated pressure (e.g., about 20 to 35 atmospheres) and with a solvent comprising: about 40 to 80% (by volume) of a water miscible lower aliphatic alcohol of 1 to 4 carbon atoms (e.g., methanol, ethanol, isopropanol or tert-butanol); 20 to 60% water; and if needed, a small amount of a strong water soluble acid, such as a mineral acid (e.g., hydrochloric, sulfuric, phosphoric or nitric acid) or an organic acid (e.g., oxalic acid, preferably acetic, formic or peroxy acids), or a small amount of a mineral salt. The solvent can further comprise recovered alcohol and alcohol/water filtrate from the process.

Figure 11:
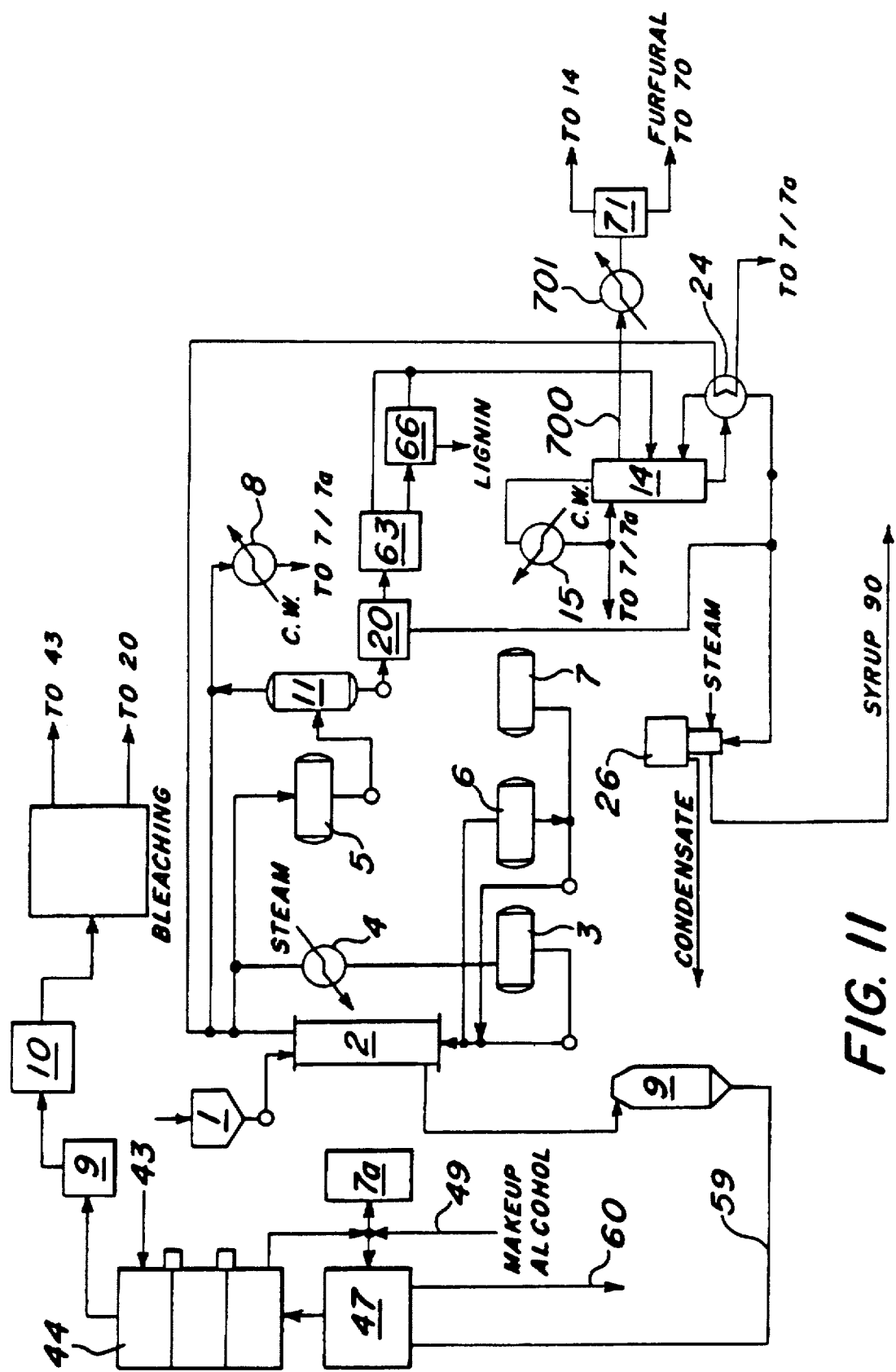
Figure 12:
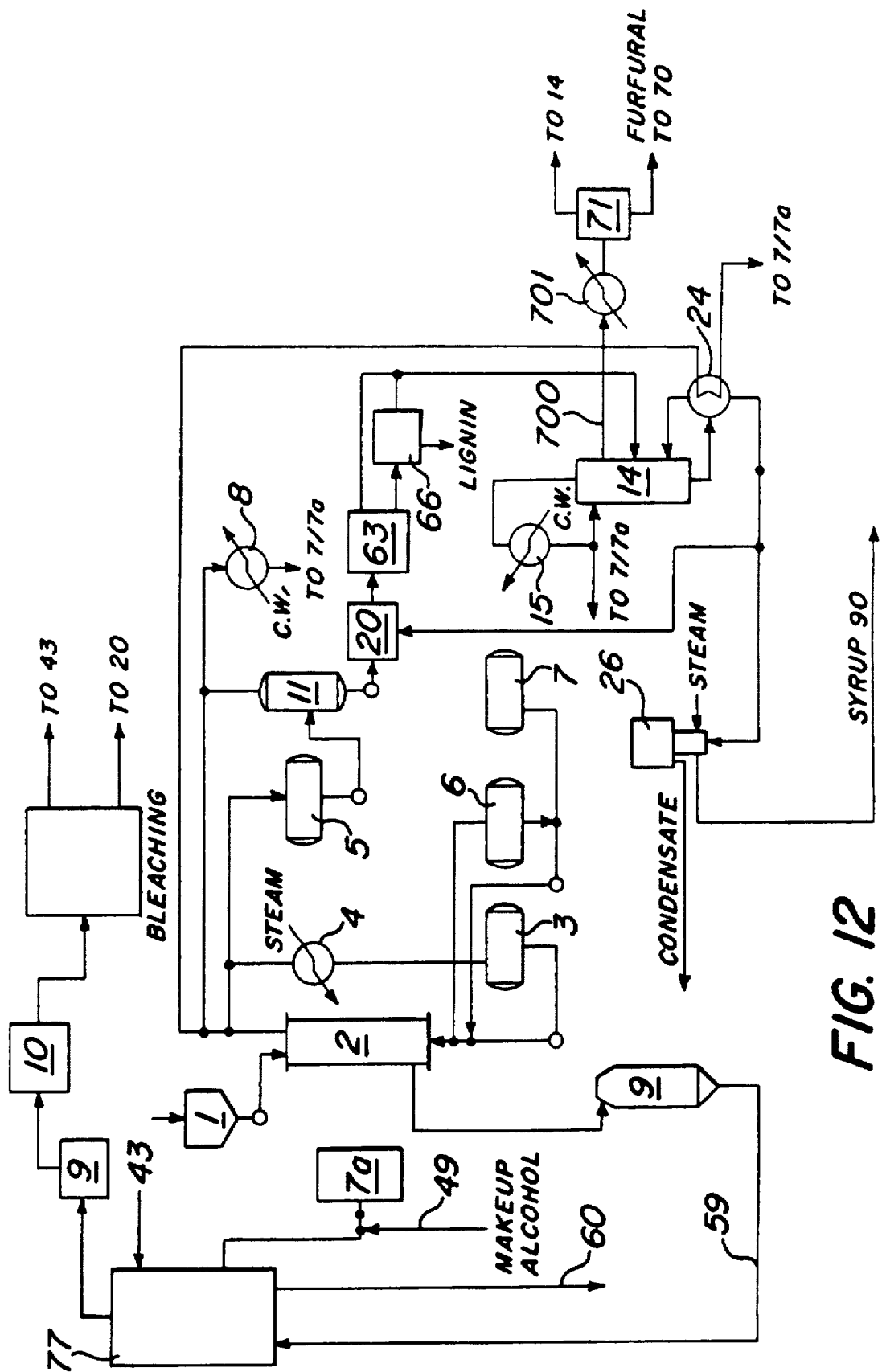

Preferably, the fibrous plant materials in the extractor 2 are preheated with low pressure steam, and then, a twice-used 60% ethanol/40% water, primary solvent from a primary solvent accumulator 3 contacts the fibrous plant materials in the extractor 2. The primary solvent is rapidly recirculated through the extractor 2 and through a peak load (e.g., steam-heated) heat exchanger 4 to raise the temperature of the fibrous plant materials to about 190° to 200° C. in a few minutes (preferably not more than about 5 minutes). Alternatively, in large scale plant operations, a time of from about 5 to 60 minutes is required. After this first pulping step is completed, the resulting extract or "black liquor" in the extractor 2 is displaced into a recovery feed accumulator 5 by a once-used 60% ethanol/40% water, secondary solvent (preferably heated to from 190° to 200° C.) from a secondary solvent accumulator 6. The black liquor which contains lignin, hemicelluloses, other saccharides and extractives (e.g., resins, organic acids, phenols and tannins) from the fibrous plant materials and the ethanol is recovered at a temperature of from about 180° to 210° C. and under a pressure of from about 20 to 35 atmospheres in the recovery feed accumulator 5. At the end of the black liquor displacement, the secondary solvent in the extractor 2 is displaced into the primary solvent accumulator 3 by a fresh 60% ethanol/40% water solvent (preferably heated to 190° to 200° C.) from a fresh solvent accumulator 7. The fresh solvent in the extractor 2 is then drained into the secondary solvent accumulator 6. Once the extractor 2 has been drained, it is vented, alcohol-rich vapors from the extractor are condensed in a water-cooled ("C.W.") condenser 8, and the resulting ethanol/water mixture from the condenser 8 is recycled to the fresh solvent accumulator 7. After venting the extractor 2, residual alcohol in the pulp in the extractor is then stripped with low pressure steam, and the resulting alcohol/water vapors are condensed and recovered as discussed below. After steam stripping, the pulp in the extractor 2 is sluiced with water, piped to a holding tank 9 and pumped through a pulp screen 10. The pulp can then be suitably subjected to conventional pulp handling, bleaching and paper-making procedures. Alternatively, as shown in FIG. 11, the steam stripping step can be omitted and after sluicing the pulp with recycled solvent to the holding tank 9, the pulp is sent through line 59 and washed in pulp washing equipment 47 (e.g. one or more pressure diffusers, drum washers belt washers) with recycled solvent from tank 7a which is a holding tank and with makeup alcohol from line 49. The pulp is cooled to a temperature below 80° C. while simultaneously additional lignin is removed and recycled through line 60 to tank 7 and the kappa number is reduced to a bleachable grade. The pulp is further washed in multistage counter-current washing equipment 44 (e.g. one or more drum washers or belt washers) by water introduction through line 43 or by introduction of bleaching filtrates and cooled to a temperature of from about 40° to 70° C. Counter-current washing equipment 44 replaces conventional, less energy efficient, steam stripping methods and removes from about 50 to about 90% additional alcohol from the pulp. Alternatively as shown in FIG. 12, the pulp can be washed on washing equipment 77 (e.g. one or more drum or belt washers) with recycled alcohol from tank 7a while simultaneously additional lignin is removed and recycled through line 60 to tank 7. The pulp is further washed on washing equipment 77 by water introduction through line 43 or bleaching filtrates and cooled to a temperature of from about 40° to 70° C. After washing of the pulp on counter-current washing equipment 44 or alternatively on washing equipment 77, the pulp is transfered to holding tank 9 and pumped through a pulp screen 10. The pulp can then be suitably subjected to conventional pulp handling, bleaching and paper-making procedures.

The extractor 2 can be loaded with another batch of fibrous plant materials from the hopper 1, and the fibrous plant materials can be contacted by the primary, secondary and fresh solvents from accumulators 3, 6 and 7 as described above.

Figure 3:
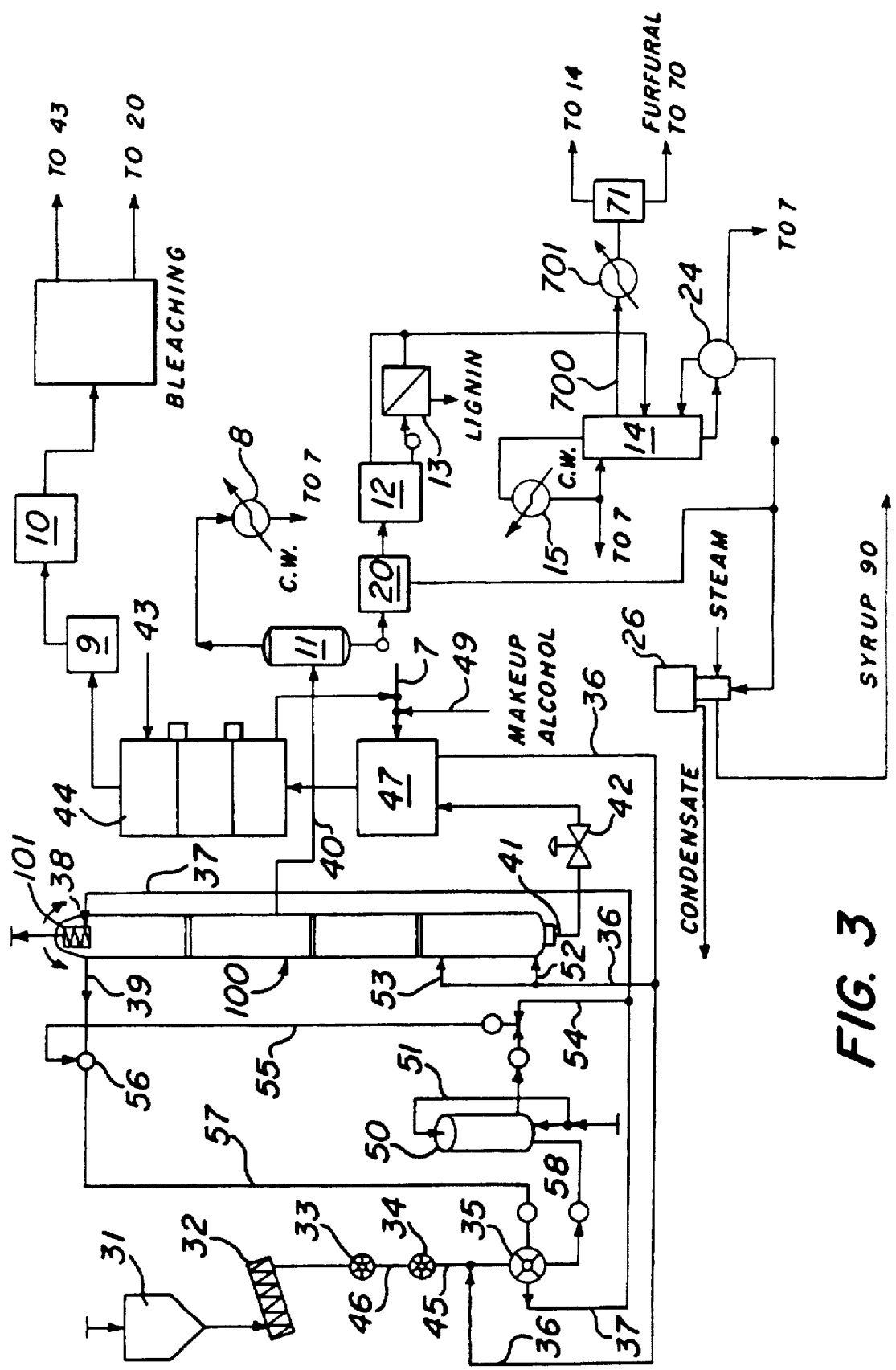
FIGS. 3, 4, 9 and 10 represent a flow chart of a continuous process for producing cellulose pulp from wood by treating the wood with an aqueous alcohol solvent and for recovering lignin, and other by-products from the alcohol/water black liquor produced in the pulping process.
Figure 4:
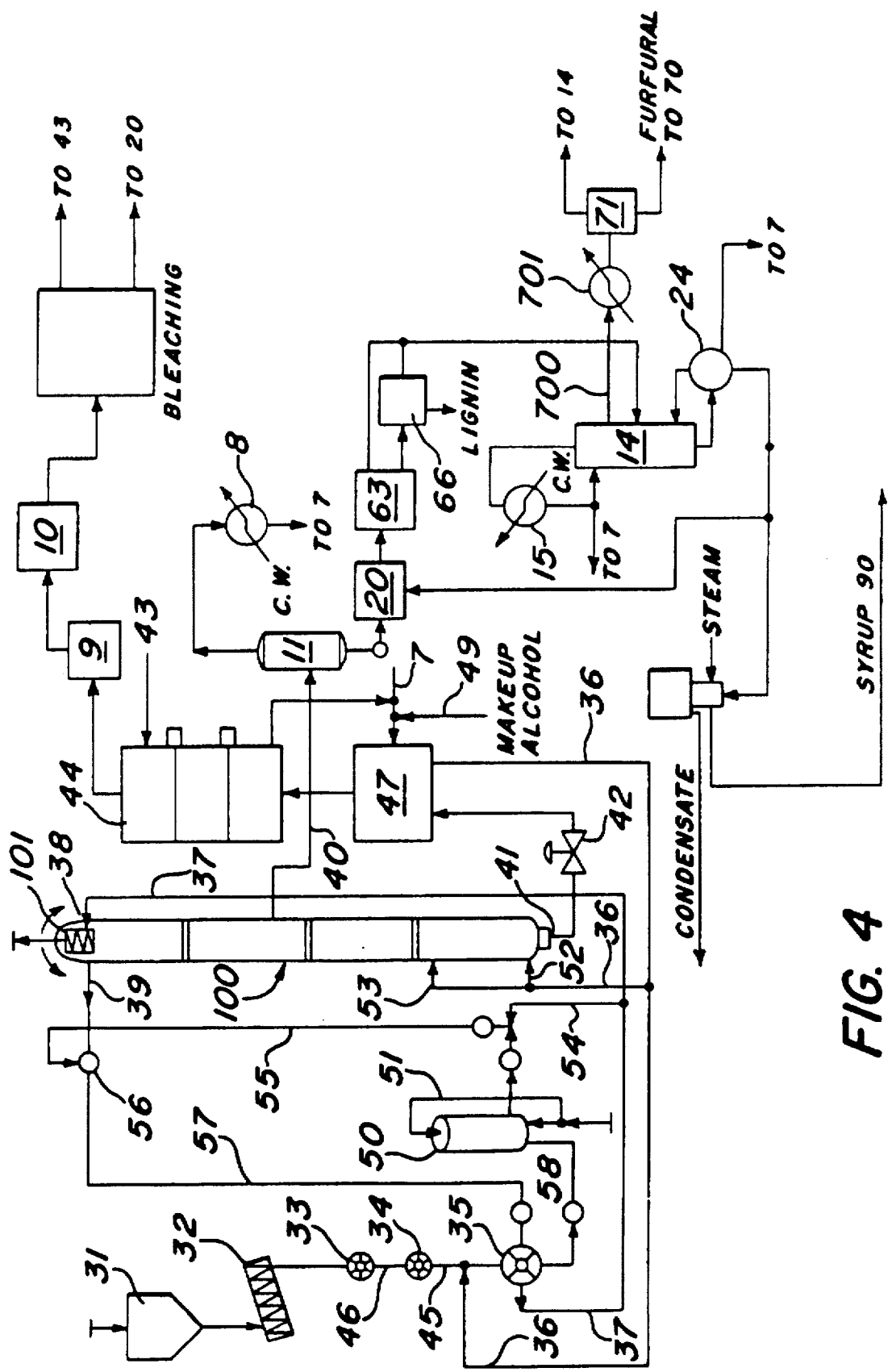
Figure 9:
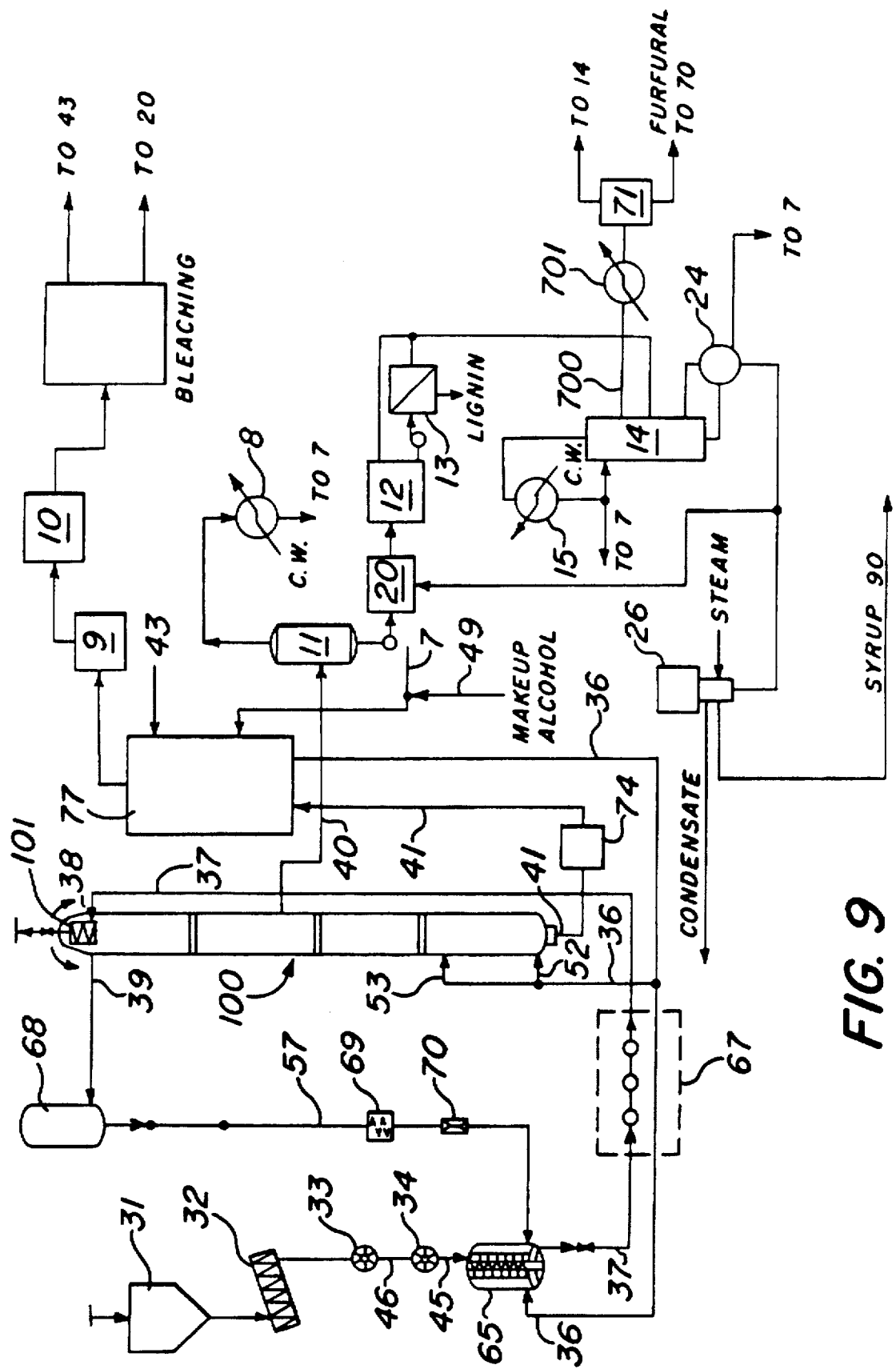
Figure 10:
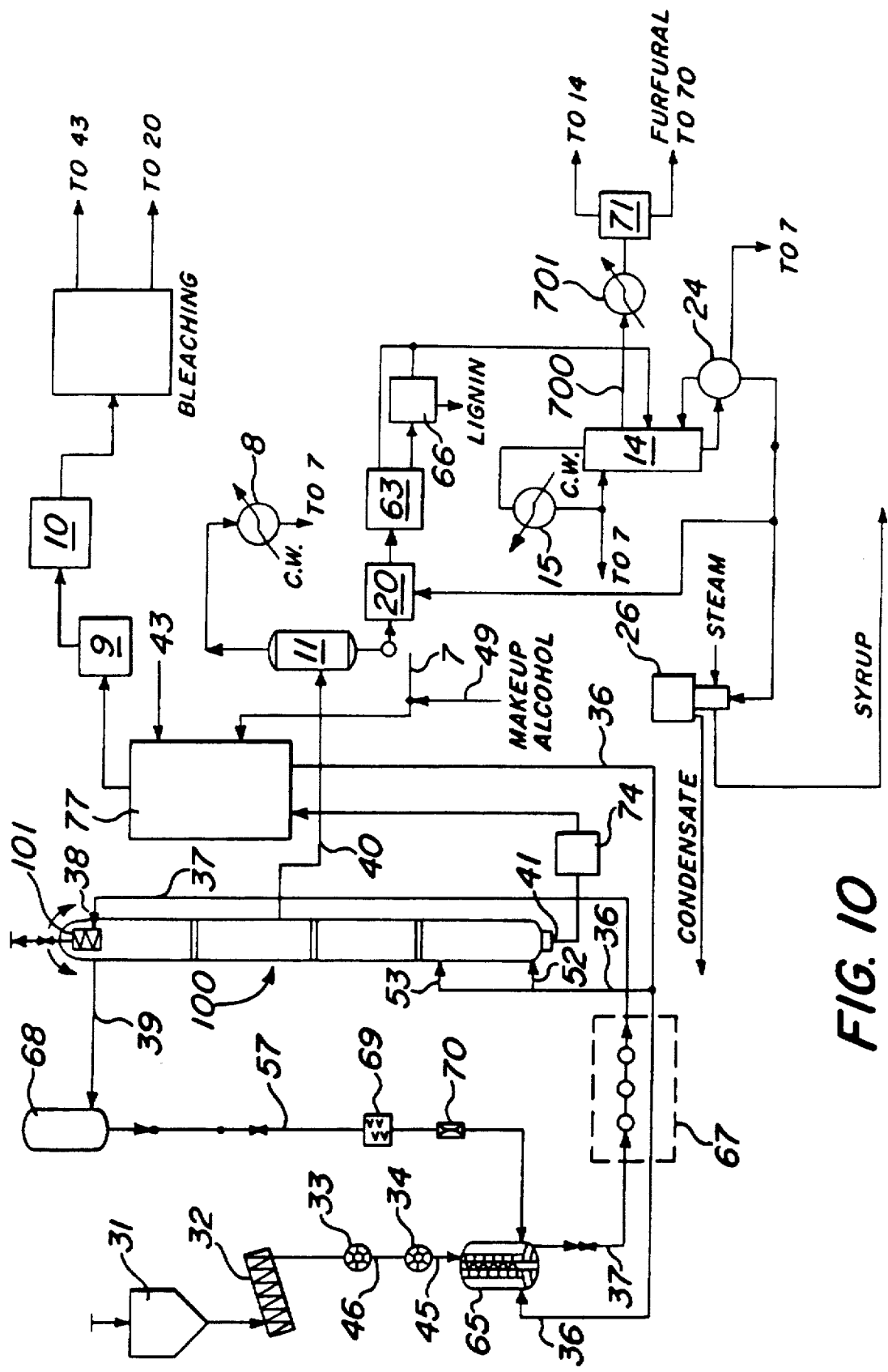

Alternatively, a continuous pulping process is shown in FIGS. 3, 4, 9 and 10. Initially, wood chips (50% moisture) or other fibrous material are pre-steamed in steaming bin 31 by injection of steam at atmospheric pressure. As shown in FIGS. 3, 4, 9 and 10 the chips are wetted and passed into metering screw 32 which can be positioned at an angle. The excess water from the steam condensates in metering screw 32 and the wet chips are passed through a first rotary valve feeder 33, heated in line 46 by direct steam injection at a temperature of from about 270° F. to about 330° F. and at a pressure of from about 30 to about 100 psig. In another embodiment, direct steam injection can be acomplished in a number of ways, for example by using a steaming vessel at a temperature of from about 200° F. to about 340° F. and at a pressure of from about 30 to about 100 psig. The steaming vessel can be equipped with a vent which can be connected to a heat exchanger, for example a water cooled condenser which can be used to condense any vapors and produce a condensate which can be returned to solvent recovery tower 14 and recycled for reuse with the solvent. Line 46 can be equipped with a steam barrier which helps prevent backup of alcohol-containing vapors into rotary valve feeder 33. The steamed fibrous plant materials are passed through a second rotary valve feeder 34 and are mixed in line 45 with a solvent from line 36 as shown in FIGS. 3 and 4. The solvent is mixed with the chips in high pressure sluice 35 or the solvent is mixed with the chips in chip sluice tank 65 as shown in FIGS. 9 and 10.

The chips are impregnated and the resultant slurry from high pressure sluice 35 or from chip sluice tank 65 passes through line 37 and enters extractor 100 at inlet 38. As shown in FIGS. 9 and 10, the slurry is pressurized through multistage centrifugal pumping system 67 which can be selected to comprise at least one centrifugal pump or several centrifugal pumps in series such that the slurry is pressurized to the operating pressure of extractor 100. As the cooking mixture enters extractor 100 at inlet 38, a liquid separator 101 regulates the flow of the mixture into extractor 100. Excess cooking mixture liquid overflows extractor 100 at outlet 39, is recycled through line 57 and pumped back into high pressure sluice 35. The excess cooking liquid from high pressure sluice 35 is pumped through line 58 and recycled back into surge tank 50. The cooking mixture in surge tank 50 is mixed internally through line 51. Any overflow cooking mixture from surge tank 50 is pumped through line 54 into line 37. In a preferred embodiment, a mechanical separator 101 is utilized to accomplish the liquid separation as described above. Additionally, mechanical separator 101 is utilized to convey the slurry of fibrous plant materials into extractor 100 in a manner which maintains the free flow of excess cooking mixture liquid. Further, mechanical separator 101 comprises movable screens to allow the adjustment of the position of such screens in mechanical separator 101 inside and relative to the top of extractor 100, as may be desirable, in view of the fibrous materials to be pulped and the pulping conditions in extractor 100.

Alternatively as shown in FIG. 9 and 10, as the excess cooking mixture liquid overflows extractor 100 at outlet 39, it is recycled through line 57. The cooking mixture liquid passes through liquid surge tank 68. Liquid surge tank 68 is equipped with a level indicator and controls the overflow level of the cooking mixture liquid. Liquid surge tank 68 can separate any noncondensable gases from the cooking mixture and can be equipped with a vent which can be connected to a heat exchanger, for example a cold water condenser. Any excess vapor from liquid surge tank 68 can be condensed and recycled to solvent recovery tower 14 and recycled for reuse with the solvent. The cooking mixture passes through line 57 into chip sluice tank 65. In one embodiment of the invention, line 57 is equipped with a heat exchanger 69 which can operate to reduce the temperature of the cooking mixture to a level such that the liquid in the cooking mixture does not flash when the cooking mixture passes through pressure reduction device 70 (e.g. a pressure reducing valve or a turbine), or when the cooking mixture passes through chip sluice tank 65. Pressure reduction device 70 can operate to reduce the pressure of the cooking mixture in line 57, namely to from 650 psig to about 20 to 650 psig. In a preferred embodiment, the pressure reduction device 70 operates to reduce the pressure in line 46 from an operating pressure within extractor 100 to a pressure slightly below the presure in line 46. When pressure reduction device 70 is a turbine, the energy which is generated can be used to operate multistage centrifugal pumping system 67. In a preferred embodiment, chip sluice tank 65 can be within the pressure range of extractor 100, namely of from about 150 to 650 psig. In another preferred embodiment, chip sluice tank 65 can be at the same pressure as in line 46. In another preferred embodiment, chip sluice tank 65 can be at a pressure lower then the pressure in line 46, such pressure being at a level low enough such that the solvent vapors do not escape into line 46.

The impregnates chips in extractor 100 are digested and extracted with solvent which is fed into extractor 100 at inlets 52 and 53. Preferably, the solvent is similar to that used in the process shown in FIG. 1. As shown in FIGS. 3, 4, 9 and 10, the solvent comprises appropriate quantities of makeup alcohol, introduced at 49, with recovered alcohol from the alcohol and by-products recovery system introduced at 7 and line 45, and with alcohol/water filtrate from counter-current washing equipment 44 or with alcohol/water filtrate from washing equipment 77. As shown in FIGS. 3 and 4, the solvent contained in line 36 is heated in pulp washing equipment 47 (e.g. one or more pressure diffusers, drum washers or belt washers) by heat exchange with the pulp leaving extractor 100 at outlet 41 or as shown in FIGS. 9 and 10, the solvent in line 36 is heated by heat exchange with the pulp on washing equipment 77.

The type of extractor used is not critical, however it should be adaptable to the continuous pulping of the cooking mixtures. Typical extractor dimensions depend on the required capacity of the extractor. For example, extractor 100 is operated in a continuous cocurrent/counter-current mode and at a pressure range of from about 150 to about 650 psig. Such an extractor is comprised of sequential reaction zones and means to add and remove solvent. The latter can be in the form of liquor extraction screens equipped with wipers or other cleaning devices that prevent screen plugging such as steam injectors.

Figure 8:
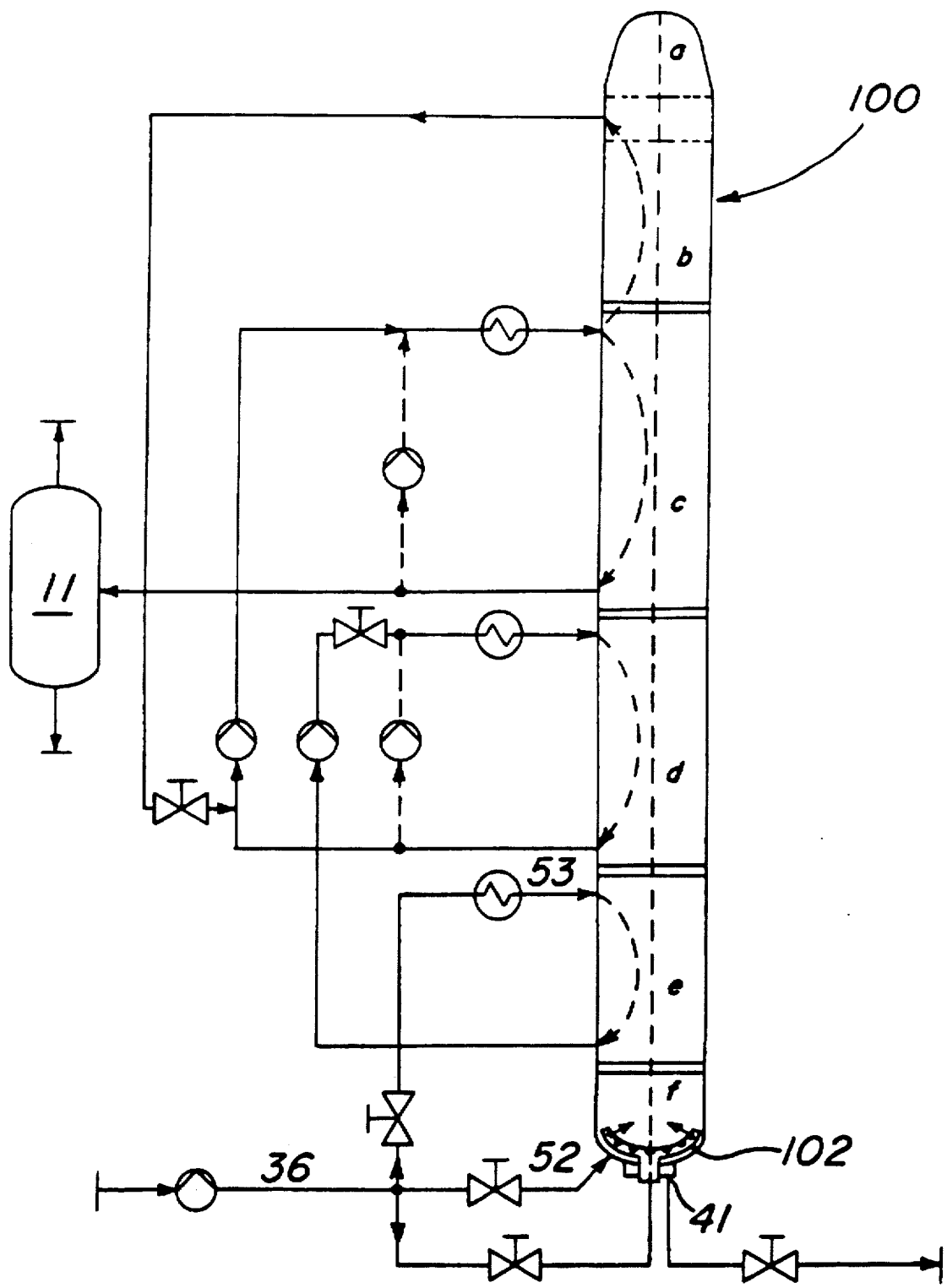
FIG. 8 is a schematic representation of a continuous extractor used in the processes of FIGS. 3, 4, 9 and 10.

In one particular extractor configuration as shown in FIG. 8, the cooking mixture which typically contains 5% chips in 95% solvent passes through extractor 100 and is exposed sequentially to six reaction zones. With this particular extractor configuration, further alcohol impregnation of the chips occurs at a constant temperature of from about 100° to 130° C. in separation zone (a) for about 2 to about 20 minutes. In separation zone (a), a vapor head space is maintained with the level of the solvent in the cooking mixture higher than the level of the chips. Any excess solvent is removed through outlet 39 and recycled as described above. The temperature of the cooking mixture chips is elevated as the cooking mixture passes into preheating zone (b) and is preheated to from about 150° to 180° C. in about 50 minutes. The heating of the cooking mixture in preheating zone (b) is achieved by circulating the cooking solvent counter-currently through a heat exchanger (typically of the tube and shell type) which is heated with steam. The heat exchanger temperature is maintained at a level sufficient to cause the cooking mixture in preheating zone (b) to heat to from about 150° to 180° C. The preheated cooking mixture is further heated in primary extraction zone (c) to from about 160° to 205° C. and subjected to digestion and extraction for about 70 minutes. The cooking mixture is heated in primary extraction zone (.c.). by circulating the cooking solvent co-currently through a heat exchanger as described above. In zone (c), a hot ethanol/water extract or "black liquor" is produced during the digestion and extraction process. The hot black liquor which contains lignin, hemicellulose, other saccharides and extractives (e.g., resins, organic acids, phenols and tannins) is separated from the cooking mixture through line 40 and subsequently treated to recover the lignin and other by-products of the pulping process.

The cooking mixture is further digested and extracted for about 60 minutes in secondary extraction zone (d) at a temperature of from about 150° to 180° C. The temperature is cooled in secondary extraction zone (d) by recirculating the cooking solvent in a heat exchanger as described above. The heat exchanger temperature is maintained at a level sufficient to achieve the cooling of the cooking mixture to maintain a temperature of from about 150° to 180° C. in secondary extraction zone (d). The cooking mixture is further digested and extracted for about 45 minutes in tertiary extraction zone (e) and the mixture is cooled to a temperature of from about 130° to 160° C. by recirculating the cooking solvent co-currently through a heat exchanger as described above. The cooking mixture is further cooled to from about 70° to 100° C. in cooling zone (f) for about 22 minutes and broken up into pulp with mixer 102. Cooling of the cooking mixture in cooling zone (f) is achieved by mixing the mixture with the solvent introduced at inlet 52 in a counter-current fashion and at inlet 53 in a co-current fashion. The solvent mixture consists of makeup alcohol, recycled alcohol from the alcohol- and by-product recovery and alcohol/water filtrate from counter-current washing equipment 44 or alternatively from washing equipment 77. The pulp exits extractor 100 through line 41.

As shown in FIGS. 3 and 4, the pulp is defiberized as the pulp passes through pressure reduction valve 42. Pressure reduction valve 42 is preferably a blow valve. The pulp is washed in pulp washing equipment 47 (e.g. one or more pressure diffusers, drum washers or belt washers) with recycled alcohol through line 7 and make-up alcohol through line 49 and cooled to a temperature below 80° C. while simultaneously additional lignin is removed and recycled through line 36 and the kappa number is reduced to a bleachable grade. The pulp is further washed in multistage counter-current washing equipment 44 by introduction of water or bleaching filtrates through line 43 and cooled to a temperature of from about 40° to 70° C. Counter-current washing equipment 44 replaces conventional, less energy efficient, steam stripping methods and removes from about 50 to about 90% additional alcohol from the pulp. Alternatively, as shown in FIGS. 9 and 10, and in connection with certain fibrous plant materials, it is believed possible to transfer the pulp through line 41 to a holding tank 74 which is at pressure sufficient to preserve pulp strength, and where possible such pressure is atmospheric. The pulp is washed on washing equipment 77 with recycled alcohol through line 7 and make-up alcohol from line 49 and cooled to a temperature below 80° C. while simultaneously additional lignin is removed and recycled through line 36. The pulp is further washed on washing equipment 77 by water introduction through line 43 or bleaching filtrates and cooled to a temperature of from about 40° to 70° C.

After washing of the pulp on counter-current washing equipment 44 or alternatively on washing equipment 77, the pulp is sent to holding tank 9 and pumped through a pulp screen 10. The pulp can then be suitably subjected to conventional pulp handling, bleaching and paper-making procedures.

In one bleaching technique, the pulp now referred to as brownstock can be delignified by treating with oxygen coupled with a prior peroxy treatment using a peroxy compound such as peracetic acid or hydrogen peroxide. Filtrates thus obtained under acidic conditions can be recycled as wash water for brown stock washing. These filtrates are introduced at inlet 43, mixed with water and become part of the solvent in line 36. Since the rate of delignification is directly proportional to the acidity of the solvent, it is believed that these acidic filtrates will accelerate the rate of delignification. It is also believed that the presence in the filtrates of organic acids of sodium lignate accelerates the rate of delignification. It is believed that such acid catalyzed delignification will result in lowering the operating temperature and pressure in extractor 100. Additionally, if several peroxy compound treatments are used sequentially, counter-current filtrates can be recycled. Alternatively, after pH adjustment, filtrates from alkaline oxygen delignification can also be used. For example, delignification of pulp with oxygen can be carried out by first mixing a pulp slurry at from about 9 to 15% consistency by weight of pulp solids with a solution of sodium hydroxide (caustic) and further mixing at high shear with oxygen gas. The amount of caustic added can preferably be from about 2 to 8%, more preferably from about 3 to 6% based on % wt/wt of oven dry (o.d.) pulp. The temperature of the reaction mixture can preferably be between about 60° C. and 110° C., more preferably between about 70° C. and 90° C., and oxygen pressure in the bleaching vessel can preferably be maintained at from about 40 to 110 psig, more preferably at from about 80 to 100 psig for oxygen delignification and at from about 32 to 60 psig for delignification using oxidative extraction. The reaction time with oxygen can preferably be from about 6 to 60 minutes, more preferably from about 40 to 50 minutes. Additional chemical agents which may be added to help preserve strength properties include 0.5% to 1% magnesium sulfate, 0.5% diethylene triamine pentaacetic acid (DTPA), and up to 3% sodium silicate. For example, peroxy treatment of pulp can be achieved by mixing peracetic acid with the pulp at a pH of about 2 to about 10 and in amounts of from about 0.5 to about 4% by weight of peracetic acid per weight of oven dried pulp. The pulp can be of any consistency, but is preferably between about 10 and 12% by weight of pulp solids. The reaction time can preferably be from about 20 minutes to about 3 hours at a temperature of from about 40° C. to 90° C. Alternatively, peroxy treatment of pulp can also be achieved by mixing hydrogen peroxide with the pulp in amounts of from about 0.5% to about 4% hydrogen peroxide and at a pH of from about 2 and 11. The pulp can be of any consistency, but is preferably between about 10% and 12% by weight of pulp solids and the temperature of the reaction can be maintained at from about 40° and 90° C. Magnesium sulfate at from about 0.5% to 1.0% may be added for viscosity protection of the pulp, and DTPA may be added at from about 0.05 to 0.5% to prevent catalytic decomposition of the peroxide by metal ions such as manganese, copper, and iron.

As shown in FIGS. 1, 3, 4, 9, 10, 11 and 12, the black liquor is flashed into a flash tank 11 to recover part of the ethanol. The flash tank 11 can be at atmospheric pressure for simplicity of operation or at reduced pressure to further cool the black liquor and enhance the alcohol recovery. The reduction in pressure in the flash tank 11 causes partial vaporization of the ethanol and leaves the residual black liquor in the flash tank with an ethanol content of about 30 to 45%, preferably about 35 to 40%. The residual black liquor is cooled during this step to a temperature of less than about 95° C., preferably down to about 80° to 92° C., but not below about 70° C. to avoid premature precipitation of lignin in the flash tank 11. The black liquor can be heated by steam injection or indirect heating before flashing in flash tank 11 to vaporize more ethanol, therefore decreasing the ethanol concentration of the liquor to from about 25 to 34% and reducing the amount of dilution water needed for precipitation by from about 20 to 70%. Steam injection or indirect heating can also be introduced directly into flash tank 11 or in any of the flash tanks that can be used in sequential series with flash tank 11. The ethanol/water vapors obtained are condensed in condenser 8 and recycled, along with any makeup ethanol, water and/or acid, for use in treating subsequent batches of fibrous plant materials. Alternatively, in the continuous process as shown in FIGS. 3, 4, 9 and 10, the ethanol/water vapors from flash tank 11 (or flash tanks in sequential series with flash tank 11) can be recycled in reboiler 24, thus providing energy for distillation in solvent recovery tower 14. Solvent recovery can be further enhanced by interfacing solvent recovery tower 14 with additional solvent recovery towers and reboilers arranged in sequential series with solvent recovery tower 14.

In accordance with this invention, lignin is then separated from the residual black liquor discharged from the flash tank 11. This step is carried out by diluting and preferably cooling the residual black liquor, as it leaves the flash tank 11, with water and acid to form a diluted residual black liquor with: a) an alcohol content of less than about 30% (by volume), preferably about 10 to 25%, particularly about 12 to 21%, with an alcohol content of about 8% being a practical minimum for subsequently recovering the alcohol economically; b) a temperature of less than about 75° C., preferably less than about 60° C., particularly about 35° to 55° C.; and c) a pH of less than about 3, preferably less than about 2.5, particularly about 1.5 to 2.5. In this step, particular temperatures are not critical, although providing higher temperatures in the diluted residual black liquor will generally increase settling rates of the lignin but will yield a darker colored lignin and may decrease its yield. About 75° C. is a maximum temperature to avoid the formation of tarry lignin precipitates, ambient temperatures (e.g., about 20° C.) is a practical minimum, although lower temperatures (e.g., down to about 0° C.) can be used if low settling rates can be tolerated. Temperatures below about 65° C., particularly below 60° C., provide a significantly lighter colored lignin precipitate. Alternatively, in large scale plant operations, about 30° C. is a maximum temperature in order to avoid the formation of tarry lignin precipitates. Also, particular pH's of the diluted residual black liquor are not critical in this step, but lower pH's increase the yield of precipitated lignin from the diluted residual black liquor and permit the use of higher temperatures in the diluted residual black liquor. However, lowering pH below about 1 provides little or no additional improvement in yield, and for this reason, a pH of about 1 is a practical minimum although lower pH's can be used. At a pH of less than about 3, lignin will precipitate from the diluted residual black liquor in high yield and at a high rate as fine solids. These lignin solids can then be separated from the remaining diluted residual black liquor supernatant in a conventional manner. Preferably, the lignin solids are separated by: allowing them to settle out as a paste of about 6 to 12% (by weight) solids in a conventional clarifier or settling tank 12; then concentrating this paste of lignin solids in a conventional centrifugal separator to form a wet cake of about 30 to 40% solids; and then drying this wet cake to form a uniform fine, free flowing powder. Alternatively, in large scale plant operations, the lignin solids are preferably separated by using large scale filters (e.g. belt filter and filter press, preferably drum filter) which allows easy washing of the lignin cake.

In diluting the residual black liquor from the flash tank 11 with the water and acid to precipitate lignin, any conventional water soluble acid can be utilized which will provide the diluted residual black liquor with a pH of less than about 3.0, preferably less than about 2.50. For example, a strong mineral acid (e.g., hydrochloric, nitric, sulfuric or phosphoric acid) or a strong organic acid (e.g., oxalic acid, preferably acetic, formic or peroxy acids) can be used. Alternatively, filtrates from the bleaching step can also be used. They can be added to the water in line 43 and alternatively, they can be added to mixing tank 20. Additionally, oxygen delignification filtrates, after pH adjustment, are able to precipitate lignin at a pH above 3.0, preferably between approximately 3.5 and approximately 4.0.

Preferably, the water and acid are mixed together before they are used to dilute the residual black liquor. In this regard, a particularly preferred mixture of acid and water is a residual black liquor supernatant that is derived from a previous batch of fibrous plant materials and that has been recycled and used to dilute the residual black liquor from the flash tank 11 after: a) the supernatant has been separated from the lignin solids from the previous batch of fibrous plant materials in the settling tank 12 and the centrifugal separator 13 as shown in FIGS. 3 and 9, or as shown in FIGS. 4, 10, 11 and 12 in large scale filter 63; and b) the alcohol content of the supernatant has been recovered in a conventional solvent condenser 15 as described below. The recycled residual black liquor supernatant or stripper bottoms, when used for diluting the residual black liquor from the flash tank 11, provides higher yields and faster settling of lignin solids precipitating in the settling tank 12 and centrifugal separator 13 as shown in FIGS. 3 and 9.

Figure 2:
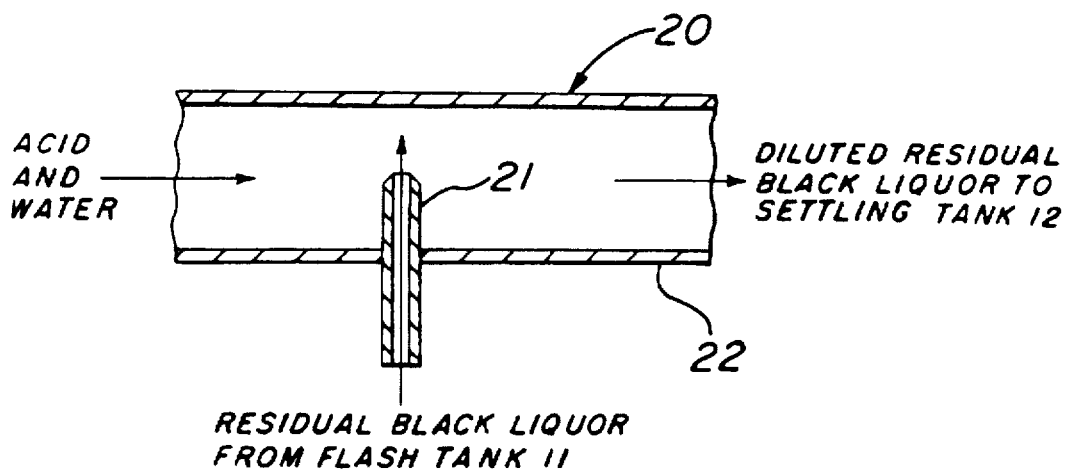
FIG. 2 is a schematic sectional view of an example of an apparatus for precipitating lignin from the alcohol/water black liquor from the processes of FIGS. 1, 3, 4, 9, 10, 11 and 12.

In precipitating lignin from the residual black liquor from the flash tank 11, the method of diluting the residual black liquor with the water and acid also is not critical, so long as there is rapid and intimate mixing of the residual black liquor with the acid and water. For example, the residual black liquor can be suitably diluted by adding it to the acid and water in a conventional static dispersion mixer or a mixing tank, generally 20. The residual black liquor can also be diluted by adding it as a finely divided stream to a stream comprising a solution of the water and acid, for example, by means of a venturi-type device, generally 20, as shown schematically in FIG. 2. The residual black liquor from flash tank 11 in FIGS. 1, 3, 4, 9, 10, 11 and 12 can be pumped through a small nozzle 21 located at about the center of a pipe 22 in the venturi-type device 20 in FIG. 2, and the acid and water solution can flow in the pipe 22 towards the settling tank 12. As the residual black liquor is injected by the nozzle 21 into the acid and water solution in the pipe 22, the residual black liquor is rapidly diluted and cooled by the acid and water in the pipe 22. Lignin rapidly precipitates as fine solids from the resulting diluted residual black liquor in the pipe 22, which solids can be easily collected and concentrated in the settling tank 12 and centrifugal separator 13. Alternatively, as shown in FIGS. 4, 10, 11 and 12, the residual black liquor exits mixing tank 20 and enters a liquid/solid separation system consisting of large scale filter 63 (e.g. belt filter, filter press, preferably drum filter), and dryer 66. Filtrates of alcohol and dissolved solids, including hemicellulose, are extracted from filter 63 to be distilled in solvent recovery tower 14. Precipitated lignin cake is discharged from filter 63 and is dried to a powder-like form in dryer 66.

In precipitating lignin in accordance with this invention, the yield and settling rates of the lignin are generally a function of: a) the wood species; b) the process conditions utilized in the extractor 2; c) the temperature, pH and solids content of (i) the residual black liquor from the flash tank 11 and (ii) the acid and water used to dilute it; and d) the ratio of residual black liquor to the acid and water used to dilute it. For example, the lignin from softwoods, such as spruce, is preferably precipitated at a temperature after dilution of about 40° to 60° C. using an acid and water solution with a pH of about 1.5 to 2.5 and with a ratio of residual black liquor to the acid and water solution of about 0.5 to about 1. For hardwoods such as aspen, it is preferred to use an acid and water solution with a pH of about 1.2 to 2.2 and a temperature after dilution of less than about 50° C. In this regard, it is preferred to use a ratio of residual black liquor to the acid and water solution of: a) about 0.2 to 0.8 if the temperature after dilution is about 40° C.; and b) about 0.6 to 1.0 if the temperature after dilution is less than about 40° C. (e.g., down to ambient temperature). For hardwoods, such as sweetgum, maple and oak, it is preferred to use a temperature after dilution of about 40° to 60° C., an acid and water solution with a pH of about 1.5 to 2.5, and a ratio of residual black liquor to the acid and water solution of about 0.35 to 0.7.

The clarified residual black liquor filtrate from the lignin solids separation step contain alcohol, furfural, wood sugars, acetic acid and low molecular weight lignin fragments that were not captured in the precipitation procedure. As shown in FIGS. 1, 3, 4, 9 10, 11 and 12, the ethanol content is preferably recovered in the solvent recovery tower 14 and solvent condenser 15. The ethanol content of the supernatant can be stripped (e.g., down to about 200 ppm) in a conventional manner in the solvent recovery tower 14 at atmospheric pressure. Preferably, the tower 14 is heated by heating and recycling a portion of the bottoms stream from the tower 14 in a heat exchanger 24 as shown in FIGS. 1, 11 and 12, using the low pressure steam used to strip residual ethanol from the pulp in the extractor 2. Alternatively, when additional recovery towers are used sequentially with solvent recovery tower 14, the tower 14 can be operated under vacuum or pressurized. The ethanol/water vapors from the tower 14 are condensed in a conventional manner in the water-cooled condenser 15 (or by heat exchange with the stripper feed) and are then recycled together with the ethanol/water mixture which condenses from the low pressure steam in the heat exchanger 24. In accordance with this invention, the ethanol content of the supernatant from the settling tank 12 and centrifugal separator 13, or alternatively from large scale filter 63 as shown in FIGS. 4 and 10, can be suitably recovered in high yield in a simple manner, without lignin precipitating within the solvent recovery tower 14 and forming tarry or gummy deposits on the internal surfaces of the tower.

The clarified residual black liquor filtrates from the lignin solids separation step typically contains from about 0.2 to 0.8% furfural, from about 10 to 15% alcohol, from about 0.5 to 10% dissolved solids, and water. As shown in FIGS. 1, 3, 4, 9, 10, 11 and 12 the black liquor is fed to solvent recovery tower 14 and a furfural side draw is removed which contains from about 12 to 30% furfural. The furfural side draw is taken at a plate above the feed plate at line 700 and comprises of from about 2 to about 4% of 2-hydroxyethylbutanoate (HEB) on a weight basis with furfural comprised in the side draw. HEB can be significantly destroyed by introducing into line 700 an acidic solution of a mineral acid, for example sulfuric acid, hydrochloric acid, and the like at a pH of from about 1 to about 2.5 and for at least 5 minutes, preferably of from about 5 to about 120 minutes and preferably at the operating temperature at line 700. Alternatively, HEB can be significantly destroyed by introducing into line 700 an alkaline solution of for example sodium hydroxide, calcium hydroxide, magnesium hydroxide, sodium carbonate, sodium bicarbonate and the like at a pH of from about 8 to about 11 and for at least 5 minutes, preferably of from about 5 to about 120 minutes at the operating temperature at line 700. The acid or alkali catalytically break down HEB into ethanol and 2-hydroxybutyric acid. The treated furfural side draw which comprises of from about 1.5 to about 3.5% 2-hydroxybutyric on a weight basis with furfural is cooled by indirect heat exchange in heat exchanger 701 to a temperature of less than about 50° C. and separates in decanter 71 into a crude furfural layer which comprises from about 60 to 75% furfural and from about 1.5 to about 3.5% 2-hydroxybutyric acid on a weight basis with furfural and an alcohol rich aqueous layer which is returned directly to solvent recovery tower 14. The crude furfural can be upgraded to from about 85 to 91% furfural using liquid/liquid extraction and can be further purified to from about 95 to 98% furfural using pervaporation. Other purification techniques include freeze concentration, dehydration, distillation and the use of a desiccant.

Figure 5:
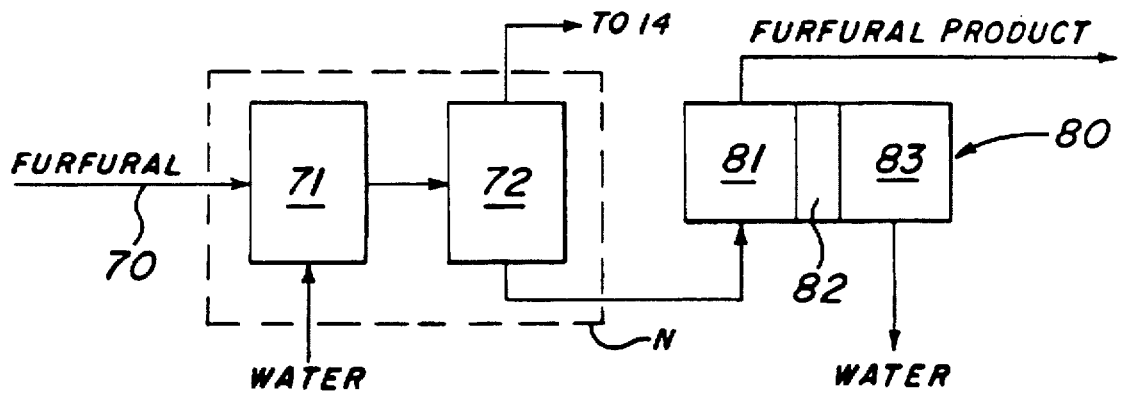
FIG. 5 is a schematic representation of crude furfural upgrading and purification by liquid/liquid cross-current extraction followed by pervaporation.

The crude furfural layer which typically contains from about 60 to 75% furfural, from about 5 to 15% ethanol, from about 0.5 to 2% methanol from about 7 to 15% water and from about 1.5 to about 3.5% of 2-hydroxybutyric acid can be upgraded using liquid/liquid extraction. Cross-current liquid extraction can be used, and as shown in FIG. 5, the crude furfural is mixed in mixer 71 using mechanical agitation with a solvent, preferably water. When the crude furfural and water separate in settler 72, a furfural raffinate and an alcohol rich water extract are obtained. Several extractions steps (N=extraction steps in FIG. 5) can be used with more than one mixer and settler arranged in sequential series. However, upgrading of the crude layer can be satisfactorily achieved with preferably two or three sequential cross-current extractions. Water and crude furfural are mixed in a volume ratio of from about 1:1 to 3:2, for about 30 minutes, and at a temperature of from about 0° to 50° C. As shown in FIG. 5, the alcohol extract which contains from about 0.5 to 6% ethanol, from about 0.2 to 1% methanol and from about 6 to 10% furfural is returned to solvent recovery tower 14. A furfural raffinate is obtained which contains from about 89 to 91% furfural, from about 0.1 to 0.2% ethanol, and from about 4.2 to 4.6% water.

Figure 6:
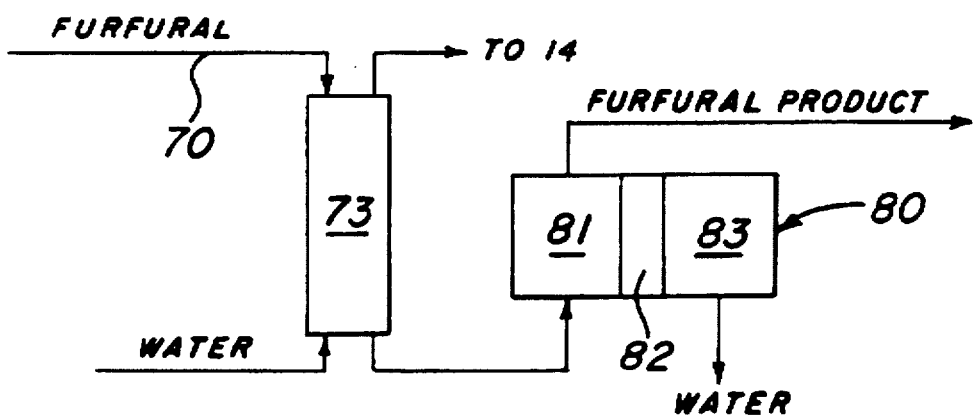
FIG. 6 is a schematic representation of crude furfural upgrading and purification by liquid/liquid counter-current extraction followed by pervaporation.

Alternatively, as shown in FIG. 6, the crude furfural can be upgraded using counter-current extraction. The crude furfural is extracted with a solvent, preferably water in counter-current extractor 73. A temperature of from about 0° to 50° C. is used, and the flow of crude furfural to water is about 3:2. An upgraded furfural raffinate is obtained which contains from about 85 to 90% furfural, from about 0.2 to 1% ethanol and from about 4 to 7% water. An aqueous alcohol extract typically containing from about 1 to 12% ethanol, from about 0.4 to 1.5% methanol and from about 6 to 10% furfural is returned to solvent recovery tower 14.

The upgraded furfural raffinate can be further purified to remove the water (e.g. by dehydration or pervaporation). FIGS. 5 and 6 are illustrative of purification by pervaporation. The pervaporation system 80 is comprised of a cell separated by a membrane 82 into two compartments 81 and 83. Membrane 82 is preferably a hydrophyllic membrane, for example, a polyvinyl alcohol membrane. The upgraded furfural is fed into compartment 81 and the water contained in the upgraded furfural is preferentially attracted by membrane 82. The water travels through membrane 82 into compartment 83. A vacuum pressure of from about 0.8 to 8 psia (preferably from about 1 to 2 psia) is maintained in tank 83 to vaporize the water. A final furfural product is obtained which contains from about 95 to 98% furfural, from about 0.1 to 0.5% ethanol and from about 0.1 to 2% water and is removed from compartment 81.

Alternatively, the crude furfural can be upgraded using conventional distillation. An upgraded furfural distillate is obtained which contains from about 95 to 99% furfural, from about 0.2 to 1% ethanol and from about 0.2 to 1% water. Although a high purity furfural distillate is obtained, upgrading and purification of furfural using liquid/liquid extraction and pervaporation is the preferred method over a single distillation since this results in an energy savings of at least two-fold and the resultant furfural product contains less ethanol and water.

The bottoms stream removed from the solvent recovery tower 14 contains wood sugars, low molecular weight lignins, acetic acid, ash and other minor components. A portion of the bottoms stream is preferably concentrated in a conventional manner, for example, in multiple effect evaporators 26. In this step, scaling or fouling of the evaporation equipment is not a significant problem because there are no substantial amounts of high molecular weight lignin in the bottoms stream from the solvent recovery tower 14. The resulting syrup, containing hemicelluloses together with small amounts of other saccharides, extractives and very low average molecular weight lignin (i.e., lignin with a molecular weight of less than about 400 g/mol), can be burned to recover its fuel value, use as animal feed, or converted to other chemical products. Alternatively, the low molecular weight lignin can be recovered. The low molecular weight lignin corresponds to lignin fragments that were not captured by the precipitation process due to their low molecular weight and water solubility and several different fractions can be isolated. In general, low molecular weight lignin can be characterized by a low average molecular weight fraction in the range of less than 600 g/mol and a low glass transition temperature in the range of from about 24° to 75° C. Another characteristic, when hardwoods are pulped, is that the low molecular weight lignin is predominantly of the syringyl type, since by nitrobenzene oxidation, it yields a syringaldehyde to vanillin molar ratio of from about 2.7:1 to about 5.3:1. This low molecular weight lignin can be used as an extender in phenolic wood adhesive systems. It can also be used in applications requiring water solubility during processing (e.g. fiberglass binders) and as an intermediate for the production of syringaldehyde and other chemicals.

Figure 7:
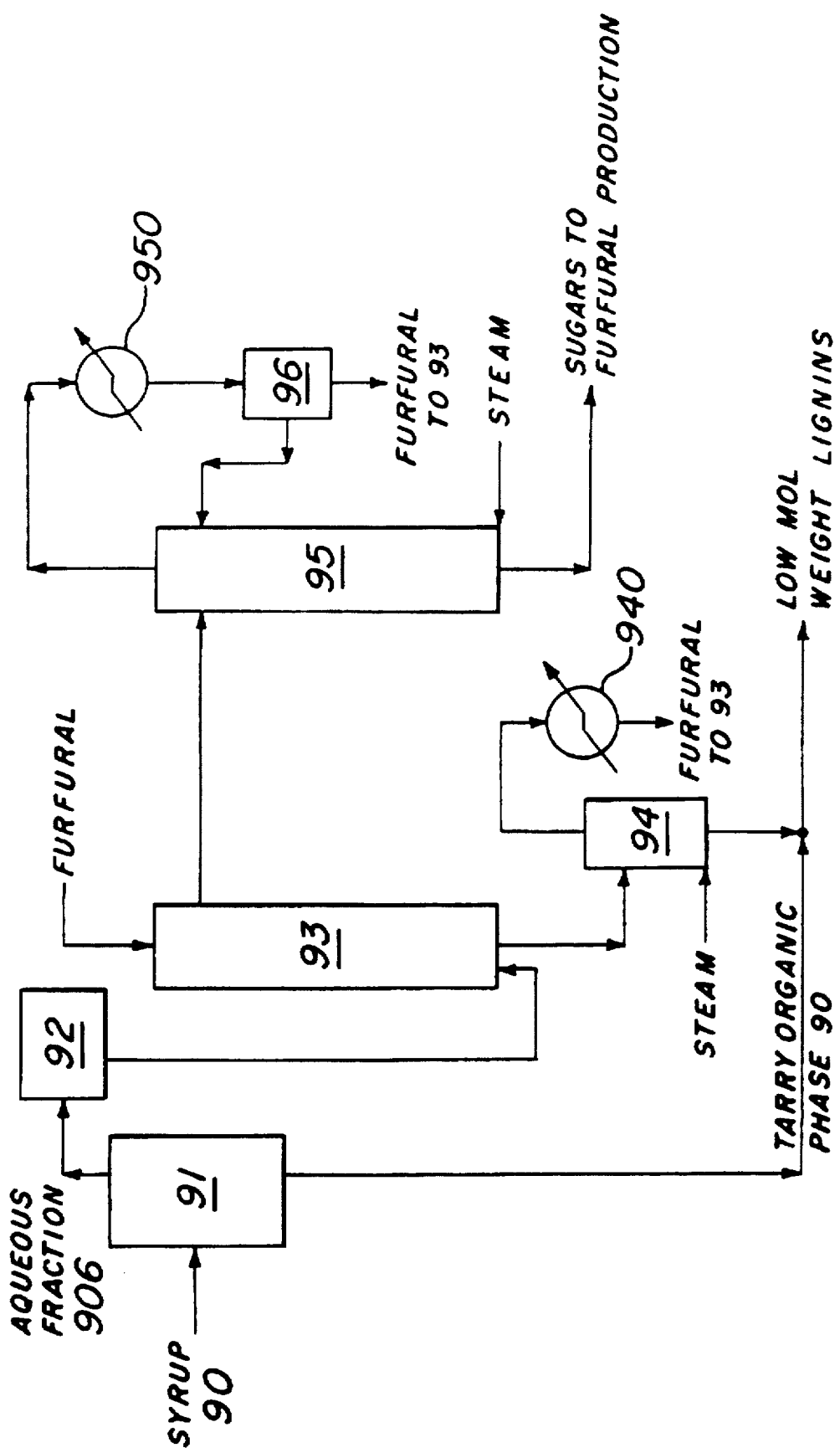
FIG. 7 is a flow chart for the recovery of low molecular weight lignin.

FIG. 7 illustrates the recovery of low molecular weight lignin. A portion of the bottom streams removed from solvent recovery tower 14 is concentrated to a syrup 90 by multiple effect evaporator 26 containing from about 10 to 30% solids. Optionally, the pH of the bottom streams is raised to a pH of from about 2.0 to about 6.0 by alkaline addition before concentrating the bottom streams. Upon concentration of the bottom streams, the low molecular weight lignin fragments form a tarry organic phase 90a which contains from about 30 to 70% of the low molecular weight lignin that was present in the bottoms stream, and an aqueous fraction 90b. This tarry organic phase 90a contains from about 60 to 90% low molecular weight lignin solids and at a temperature of from about 60° to 95° C., it has a viscosity of from about 400 to 3000 cps. This organic phase is separated in decanter 91 from aqueous fraction 90b. The aqueous fraction 90b containing the remaining low molecular weight lignin is concentrated in evaporator 92 to from about 40 to 65% solids, and is extracted with an organic solvent (preferably 1:1 volume ratio) in counter-current liquid/liquid extraction column 93. Organic solvents such as diethyl ether, cyclohexane, furan, and 3-hexanol can be used, however furfural is a particularly preferred solvent since it removes in excess of 70% of the low molecular weight lignin present in the aqueous phase in a single extraction. The furfural obtained by upgrading and purification as shown in FIGS. 5 and 6 can also be used to extract the low molecular weight lignin as described above. The raffinate from column 93 contains from about 5 to 20%. low molecular weight lignin, from about 70 to 85% furfural and from about 5 to 15% water. The raffinate is vacuum distilled in column 94. The bottoms stream from column 94 contain low molecular weight lignin and the condensate from condenser 94O containing primarily from about 85 to 95% furfural and from about 5 to 15% water is recycled to column 93. The extract from column 93 containing from about 6 to 10% furfural, from about 4 to 5% sugars and from about 50 to 80% water is stripped from furfural in column 95. The condensate from column 95 in condenser 95O is decanted in decanter 96 and the heavy layer containing from about 85 to 95% furfural and from about 5 to 15% water is recycled to column 93. The stripper bottoms from column 95 contain sugars, mostly xylose, which can be further used for furfural production by acid catalyzed dehydration.

A second portion of the bottoms stream removed from the tower 14 is preferably used as the acid and water solution for diluting the residual black liquor from the flash tank 11 in order to precipitate lignin therefrom. In this regard, the second portion of the bottoms stream from the tower 14 is preferably cooled to a temperature of less than about 50° C., preferably about 25° to 40° C. (about 0° C. being a practical minimum), and its pH is adjusted, if necessary, to about 1.0 to 3.0 by adding a strong water soluble acid to it. Then the cooled and acidified second portion of the bottoms stream (hereinbefore called the "recycled residual black liquor supernatant") is intimately and rapidly mixed (e.g., in the venturi-type device 20 of FIG. 2) with the residual black liquor to dilute and cool the residual black liquor and precipitate lignin.

The very pure lignin, which precipitates as fine solids from the diluted residual black liquor in the settling tank 12, can be subsequently removed from the centrifugal separator 13, or alternatively from large scale filter 63 as shown in FIGS. 4, 10, 11 and 12, water-washed and dried in a conventional manner (e.g., by spin flash drying) to form a fine uniform, free flowing, water insoluble powder. This lignin can be characterized as having: a relatively low number average molecular weight of about 700 to 1500 g/mol, preferably about 900 to 1300 g/mol, more preferably about 800 to 1000 g/mol, and a glass transition temperature which is preferably about 80° C. to 170° C., preferably about 130° to 150° C., particularly about 80° C. to 120° C., and more particularly about 80° C. to 95° C. although a glass transition temperature of about 70° to 150° C., is also observed; a narrow molecular weight distribution, i.e., a polydispersity of less than about 4, preferably no more than about 3, particularly only about 1.5 to 2.7; and a methoxyl content approximately equal to the methoxyl content of native lignin (i.e., about 20% for hardwoods and about 14% for softwoods). This lignin also has a softening temperature which is preferably about 120° to 150° C., particularly about 125° to 150° C. and more particularly about 130° to 135° C. These characteristics show, inter alia, the purity and low degree of chemical modification of the lignin of this invention. This lignin can be used for example, as a phenol formaldehyde resin extender in the manufacture of particle board and plywood. This lignin can also be used in the manufacture of molding compounds, urethane and epoxy resins, antioxidants, controlled-release agents and flow control agents.

This invention and many of its attendant advantages will be understood from the foregoing description, and it will be apparent that various modifications and changes can be made without departing from the spirit and scope of the invention or sacrificing all of its material advantages, the processes hereinbefore described being merely preferred embodiments. For example, the process for precipitating the lignin of this invention can alternatively be carried out by separately adding an acid and water to a solution of lignin dissolved in a water miscible organic solvent to form a diluted aqueous solution with a pH of less than about 3, an organic solvent content of less than about 30% and a temperature of less than about 75° C., from which diluted solution the lignin will precipitate as uniform fine solids. In this regard, the acid can be separately added to the residual black liquor from the flash tank 11 in FIG. 1 by adding the acid to the primary solvent from the primary solvent accumulator 3 before the primary solvent is used in the extractor 2 for pulping fibrous plant materials to produce the black liquor (which becomes, after removal of ethanol in the flash tank 11, the residual black liquor). Also, the process of this invention can be carried out with a water miscible organic solvent other than a lower aliphatic alcohol (preferably ethanol), such as acetone, glycol or glycerol, or with a mixture of such solvents. Also, these processes can be carried out using any fibrous plant material, such a bamboo, bagasse, kenaf, cereal straws, and not just wood.

We claim:

1. A method for recovering furfural from black liquor produced when fibrous plant material is pulped in a water miscible organic solvent, said method comprising the steps of:

processing said black liquor to produce black liquor filtrates including said furfural;

removing a furfural-containing draw from said black liquor filtrates;

cooling said furfural-containing draw and producing a crude furfural layer and an alcohol rich layer;

separating said crude furfural layer from said alcohol rich layer;

extracting said crude furfural layer with a solvent and producing a furfural raffinate and an alcohol containing extract;

purifying said furfural raffinate; and recovering furfural product from said purified furfural raffinate.

2. The method of claim 1 further comprising the steps of:

recovering alcohol from at least one of said alcohol rich layer and said alcohol containing extract; and recycling said recovered alcohol and combining said recycled recovered alcohol with said water miscible organic solvent for use in pulping said fibrous plant materials.

3. The method of claim 1 wherein said furfural product comprises from about 95 to 99% furfural.

4. The method of claim 1 wherein all steps are practiced continuously.

* * * * *